(12) United States Patent
Liang et al.

(10) Patent No.: US 6,280,977 B1
(45) Date of Patent: Aug. 28, 2001

(54) METHOD FOR GENERATING TRANSCRIPTIONALLY ACTIVE DNA FRAGMENTS

(75) Inventors: Xiaowu Liang, La Jolla; Philip L. Felgner, Rancho Santa Fe, both of CA (US)

(73) Assignee: Gene Therapy Systems, San Diego, CA (US)

( * ) Notice: Subject to any disclaimer, the term of this patent is extended or adjusted under 35 U.S.C. 154(b) by 0 days.

(21) Appl. No.: 09/535,262

(22) Filed: Mar. 23, 2000

Related U.S. Application Data
(60) Provisional application No. 60/125,953, filed on Mar. 24, 1999.

(51) Int. Cl.[7] .................... C12P 19/34; C12N 15/63; A61K 48/00
(52) U.S. Cl. .................. 435/91.2; 435/6; 435/320.1; 435/91.1; 514/44
(58) Field of Search ................... 435/91.2, 91.1, 435/6, 320.1; 514/44

(56) References Cited

U.S. PATENT DOCUMENTS

| | | | |
|---|---|---|---|
| 4,897,355 | 1/1990 | Eppstein et al. | 435/240.2 |
| 5,459,127 | 10/1995 | Felgner et al. | 514/7 |
| 5,561,053 | 10/1996 | Crowley | 435/69.1 |
| 5,621,080 | 4/1997 | Lin | 530/350 |
| 6,165,720 | * 12/2000 | Felgner et al. | 435/6 |

OTHER PUBLICATIONS

Clark, J. M., *Nucleic Acids Research*, 16(20):9677–9686, 1988, "Novel Non–templated Nucleotide Addition reactions Catalyzed by Procaryotic and Eucaryotic DNA Polymerases."

Li et al., Delivery of a PCR amplified DNA fragment into cells: a model for using synthetic genes for gene therapy, *Gene Therapy* 4:449–454 (1997).

Skyes, et al., Linear expression elements: a rapid, in vivo, method to screen for gene functions, *Nature Biotechnology* 17:355–359 (1999).

Almarsson, et al., "Peptide nucleic acid (PNA) conformation and polymorphism in PNA–DNA and PNA–RNA hybrids," *Proc. Natl. Acad. Sci. USA* 90:9542–9546 (1993).

Bentin, et al., "Enhanced Peptide Nucleic Acid Binding to Supercoiled DNA: Possible Implications for DNA "Breathing" Dynamics," *Biochem.* 35:8863–8869 (1996).

Demidov, et al., "Stability of peptide nucleic acids in human serum and cellular extracts," *Biochem. Pharmacology* 48(6):1310–1313 (1994).

Demidov, et al., "Kinetics and mechanism of polyamide ("peptide") nucleic acid binding to duplex DNA," *Proc. Natl. Acad. Sci. USA* 92:2637–2641 (1995).

(List continued on next page.)

*Primary Examiner*—W. Gary Jones
*Assistant Examiner*—Juliet Einsmann
(74) *Attorney, Agent, or Firm*—Knobbe, Martens, Olson & Bear LLP

(57) ABSTRACT

A method for producing transcriptionally active DNA molecules, comprising (PCR) amplification of said DNA molecule in the presence of a first DNA fragment (F1), second DNA fragment (F2), first primer (P1), a second primer (P2), a third primer (P3), and a fourth primer (P4) wherein: F1 comprises a promoter sequence; F2 comprises a terminator sequence; P1 is complementary to the 5' end of F1; P2 is complementary to the 5' end of F2; P3 comprises a first region complementary to the 3' end of F1 and a second region complementary to the 5' end of said DNA molecule; P4 comprises a first region complementary to the 3' end of F2 and a second region complementary to the 3' end of said DNA molecule.

12 Claims, 3 Drawing Sheets

OTHER PUBLICATIONS

Egholm, et al., "Recognition of Guanine and Adenine in DNA by Cytosine and Thymine Containing Peptide Nucleic Acids (PNA)," *J. Am. Chem. Soc.* 114:9677–9678 (1992).

Egholm, et al., "PNA hybridizes to complementary oligonucleotides obeying the Watson–Crick hydrogen-bonding rules," *Nature* 365:566–568 (1993).

Egholm, et al., "Efficient pH–independent sequence–specific DNA binding by pseudoisocytosine–containing bis–PNA," *Nucleic Acids Research* 23(2):217–222 (1995).

Fakhfahk, et al., "Cell–free cloning and biolistic inoculation of an infectious cDNA of potato virus Y," *J. of Gen. Virology* 77:519–523 (1996).

Felgner, et al., "Nomenclature for Synthetic Gene Delivery Systems," *Human Gene Therapy* 8:511–512 (1997).

Griffith, et al., "Single and Bis Peptide Nucleic Acids as Triplexing Agents: Binding and Stoichiometry," *J. Am. Chem. Soc.* 117:831–832 (1995).

Higuchi, R., "Recombinant PCR," *PCR Protocols: A Guide to Methods and Applications* New York Academic Press p. 177–183 (1990).

Ido, et al., "Construction of T–Tailed Vectors Derived from a pUC Plasmid: a Rapid System for Direct Cloning of Unmodified PCR Products," *Biosci. Biotech. Biochem.* 61(10):1766–1767 (1997).

Nielsen, et al., "Sequence–Selective Recognition of DNA by Strand Displacement with a Thymine–Substituted Polyamide," *Science* 254:1497–1500 (1991).

\* cited by examiner

* in excess amount

METHOD FOR GENERATING TRANSCRIPTIONALLY ACTIVE DNA FRAGMENTS

RELATED APPLICATIONS

This application claims priority under 35 U.S.C. §119(e) to U.S. Provisional Application Serial No. 60/125,953, filed Mar. 24, 1999.

BACKGROUND OF THE INVENTION

1. Field of the Invention

The present invention relates to a method for generating transcriptionally active DNA fragments. More specifically, the method relates to synthesis of a DNA fragment by polymerase chain reaction (PCR) using nested primers, promoter sequences and terminator sequences.

2. Description of the Related Art

In addition to the tremendous progress made in the past few years in sequencing the human genome, efforts have also been made to sequence other organisms that are of biomedical importance. For example, complete genomic sequences have been obtained for *Borrelia burgdorferi* (cause of Lyme disease), Chlamydia, *Heliobacter pylori* and *Mycobacterium tuberculosis*. The fast-growing sequence information provides immense opportunities to reveal the basic biology of related organisms at the gene/molecular level and to develop novel therapeutics or vaccines against various pathogens.

However, this vast sequence information also mandates a much more efficient and streamlined way to screen and identify genes of interest from tens of thousands of candidate genes. The conventional approach to gene screening and identification involves generation of a cDNA library, subcloning the DNA inserts into plasmid vectors (expression vectors), purifying plasmid DNA from bacteria for each individual cDNA clone and transfecting animal cells or tissues for functional analysis of the encoded gene product. This method, even in conjunction with the use of polymerase chain reaction (PCR) to generate cDNA fragments to allow directional and in-frame cloning, is still time consuming, costly and difficult to automate.

The present invention provides a simple, rapid method for the generation of transcriptionally active DNA fragments.

SUMMARY OF THE INVENTION

One embodiment of the present invention is a method for generating a transcriptionally active DNA molecule, comprising polymerase chain reaction (PCR) amplification of said DNA molecule in the presence of a first DNA fragment (F1), second DNA fragment (F2), first primer (P1), a second primer (P2), a third primer (P3) and a fourth primer (P4) wherein: F1 comprises a promoter sequence; F2 comprises a terminator sequence; P1 is complementary to the 5' end of F1; P2 is complementary to the 3' end of F2; P3 comprises a first region complementary to the 3' end of F1 and a second region complementary to the 5' end of said DNA molecule; P4 comprises a first region complementary to the 5' end of F2 and a second region complementary to the 3' end of said DNA molecule, whereby a transcriptionally active DNA molecule is produced by said PCR amplification. Preferably, F1 is the cytomegalovirus IE promoter. In one aspect of this preferred embodiment, the transcriptionally active DNA molecule encodes a therapeutic gene. The method may further comprise the step of adding a PNA tail to the 5'-end of P1 and P2 prior to the PCR amplification. Preferably, a thymidine base immediately precedes the region of complementarity between the third primer P3 and the first DNA fragment F1. In another aspect of this preferred embodiment, a thymidine base immediately precedes the region of complementarity between the fourth primer P3 and the second DNA fragment F2. The method may also further comprise the step of adding a PNA clamp to said transcriptionally active DNA molecule after said PCR amplification. Preferably, the method further comprises the step of adding a PNA molecule via a linker (PNA clamp tail) to primers P1 and P2 prior to the PCR amplification.

DETAILED DESCRIPTION OF THE PREFERRED EMBODIMENTS

The present invention provides a simple, efficient method for generating transcriptionally active DNA fragments which can be readily transfected into animal cells or tissues by conventional nucleic acid transfection techniques, without the need for subcloning into expression vectors and purification of plasmid DNA from bacteria. The transcriptionally active DNA fragments are synthesized by polymerase chain reaction (PCR) amplification of any gene of interest using nested oligonucleotide primers and two DNA fragments, one of which comprises an active transcription promoter sequence and one of which comprises a basic transcription terminator element.

Figure 1:
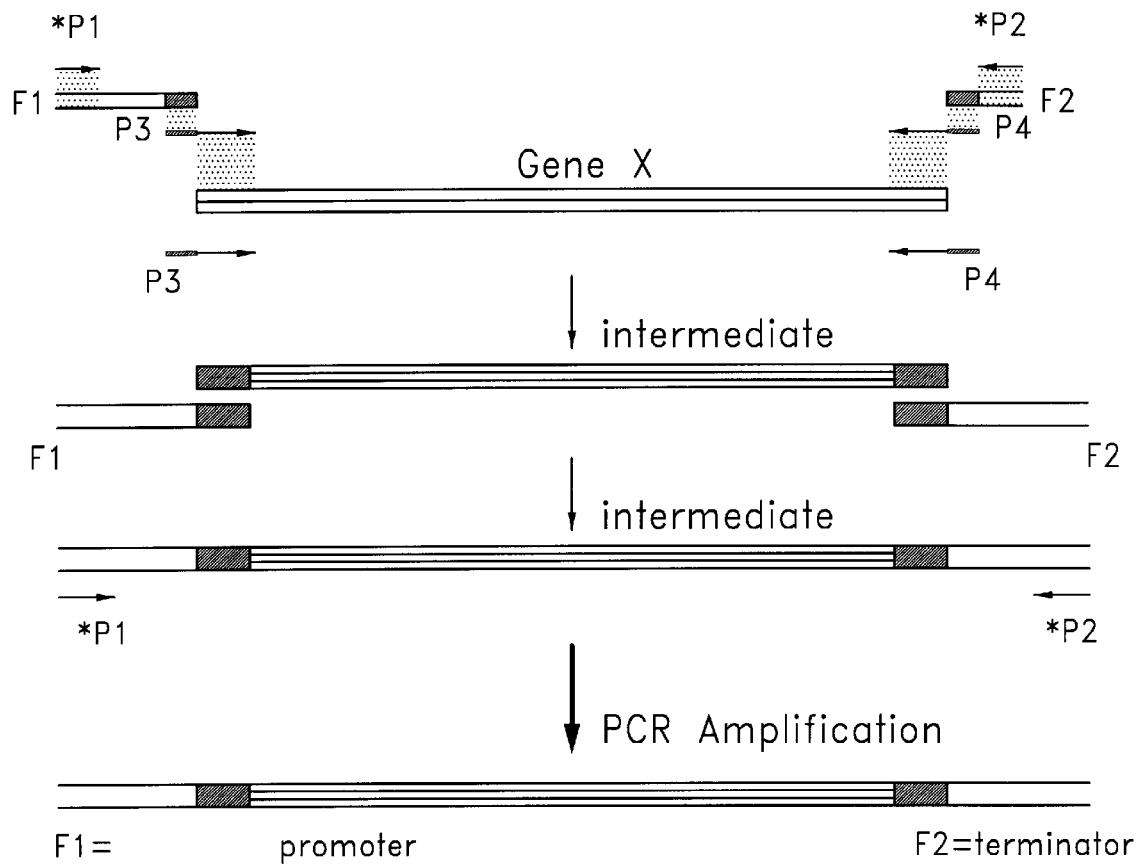
FIG. 1 is a schematic diagram of the gene amplification method of the present invention. Oligonucleotide primers P1 and P2 are complementary to the 5' end of a promoter sequence (F1) and the 3' end of a terminator sequence (F2), respectively. P3 and P4 are oligonucleotide primers which contain regions complementary to opposite ends of Gene X. In addition, P3 and P4 contain regions which are complementary to the 3' region of F1 and the 5' region of F2. An excess amount of primers P1 and P2 are combined with Gene X, or with a mixture of DNA containing Gene X, and with F1, F2, P3 and P4, or with a mixture of DNA containing F1, F2 and Gene X which has been PCR amplified using P3 and P4, and subjected to PCR to produce a transcriptionally active linear DNA fragment containing F1, F2 and gene X.
Figure 3:
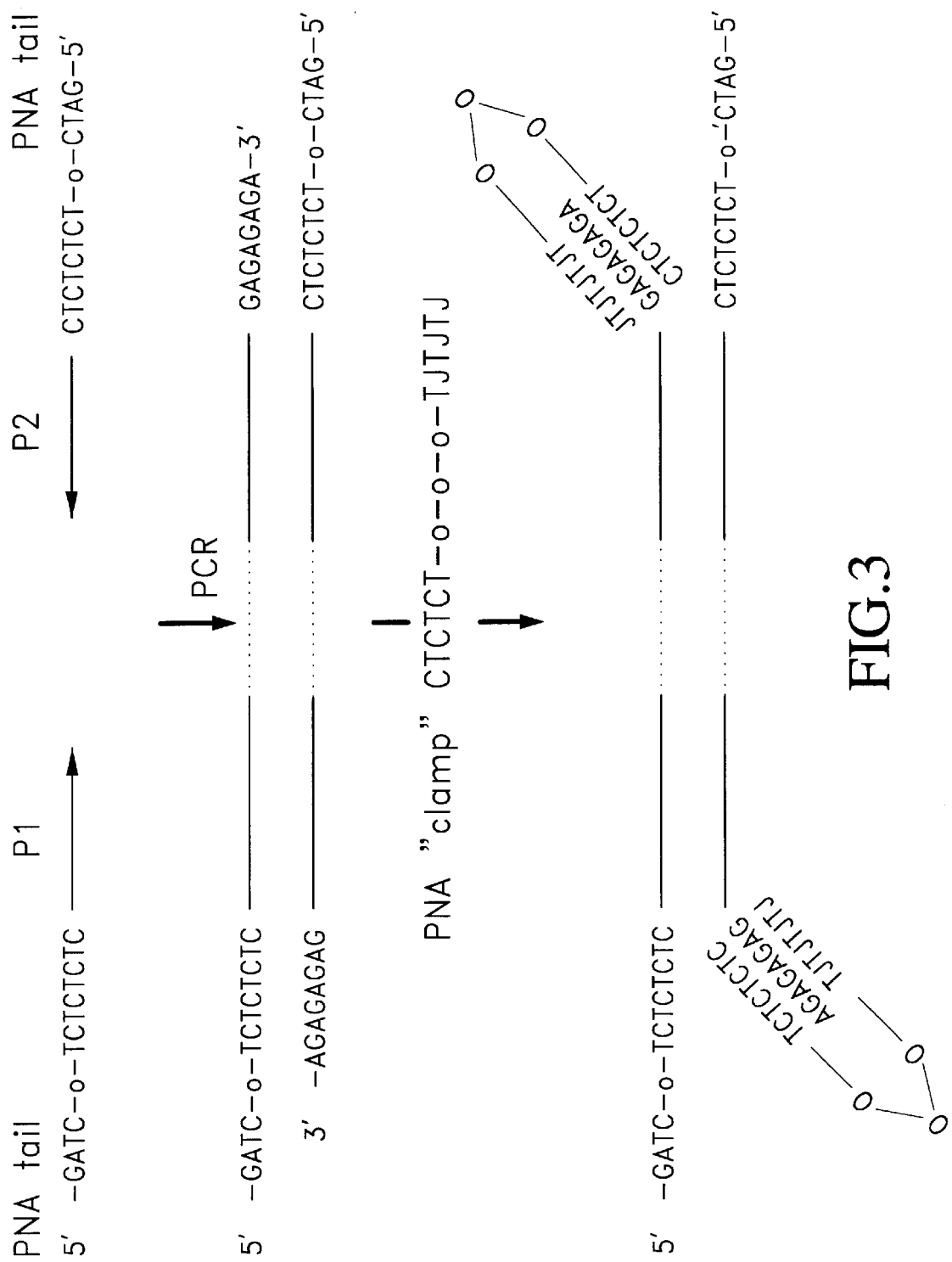
FIG. 3 is a schematic diagram showing the use of peptide nucleic acid (PNA) sequences and PNA clamps to protect the ends of linear expression DNA fragments. Primers P1 and P2 contain a PNA tail which is resistant to proteolytic and exonuclease degradation. The resulting linear expression DNA fragment contains a PNA tail at each of the 5'-ends. The 3' ends are protected by addition of a PNA "clamp" which is also resistant to proteolytic and exonuclease degradation.
Figure 4:
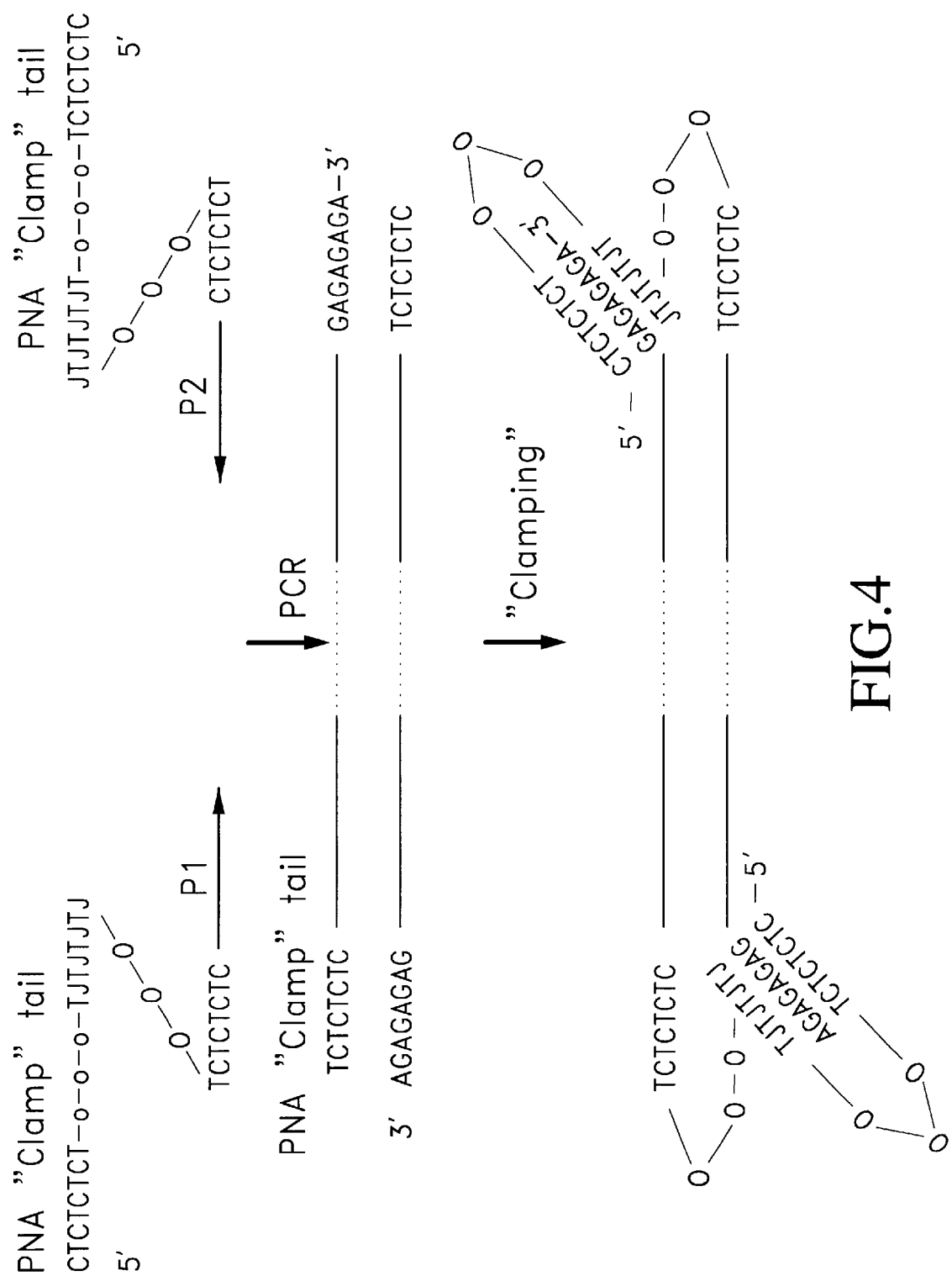
FIG. 4 is a schematic diagram showing the use of a PNA "clamp" tail to protect the 5' ends of the linear expression DNA fragment, followed by formation of a clamp during PCR to protect the 3' ends.

A first primer is complementary to the DNA fragment comprising the promoter; a second primer is complementary to the DNA fragment comprising the terminator; a third primer is complementary to both the promoter sequence and one end of the gene of interest; and a fourth primer is complementary to both the terminator sequence and the other end of the gene of interest. These promoters, genes and terminators are linked in an expression cassette as shown in FIG. 1. In addition, the ends of linear DNA containing the expression cassette can be protected from exonuclease digestion during and after transfection by incorporating peptide nucleic acid (PNA) sequences and PNA clamps as shown in FIGS. 3 and 4.

As used herein, the term "promoter" is a DNA sequence which extends upstream from the transcription initiation site and is involved in binding of RNA polymerase. The promoter may contain several short (<10 base pair) sequence elements that bind transcription factors, generally dispersed over >200 base pairs. A promoter that contains only elements recognized by general and upstream factors is usually transcribed in any cell type. Such promoters may be responsible for expression of cellular genes that are constitutively expressed (sometimes called housekeeping genes). There are also tissue-specific promoters limited to particular cell types, such as the human metallothionein (MT) promoter which is upregulated by heavy metal ions and glucocorticoids.

As used herein, the term "terminator" is a DNA sequence represented at the end of the transcript that causes RNA polymerase to terminate transcription. This occurs at a discrete site downstream of the mature 3' end which is generated by cleavage and polyadenylation.

The present method can be used to quickly generate nuclease-resistant and transcriptionally active linear DNA molecules which express any desired gene with any known sequence. The linear DNA can then be delivered into animal cells or tissues for functional analysis, vaccination and other pharmaceutical applications. This method also avoids problems associated with bacterial growth such as toxicity and stability. This method can also be completely automated for use in high-throughput screening methods.

Referring now to FIG. 1, oligonucleotide primers P1 and P2 are complementary to the 5' region of DNA fragments F1 and F2, respectively. Fragment F1 comprises a transcription promoter (darkened region) and fragment F2 comprises a transcription terminator (darkened region). Primers P3 and P4 are complementary to the 3' ends of F1 and F2, respectively, and to different ends of the DNA fragment containing Gene X. FIG. 1 shows the putative intermediates and the final product which are formed in the present PCR-based method when P1, P2, P3, P4, F1 and F2 are added to a DNA template comprising Gene X. It should be noted that amount of primers P1 and P2 present in the reaction mixture are preferably at least about 100 fold greater than the amounts of P3, P4, F1 and F2, to minimized the amounts of intermediate products generated during the reaction. To generate the first intermediate, primer P3 and P4 are used which amplify from the promoter and terminator sequences of F1 and F2 across Gene X, resulting in an intermediate having the promoter and terminator sequences on the ends and Gene X in between these sequences.

The second intermediate is formed by hybridization of the first intermediate with fragments F1 and F2 via their complementary promoter and terminator sequences (darkened regions), followed by PCR amplification from primers P3 and P4, resulting in a DNA segment comprising the entire F1, F2 and Gene X.

In the last step of the reaction, PCR amplification of the second intermediate using primers P1 and P2 results in amplified amounts of the complete transcriptionally active DNA fragment.

The method of the invention may be performed by adding all of the components in a single reaction mixture. Alternatively, two separate PCR reactions can be performed. In the first reaction, the template gene, P3 and P4 are used first. The product of this reaction is then used as a template for a second PCR reaction involving fragments F1 and F2, plus primers P1 and P2.

The generation of final products using the nested PCR method describe above is dependent on the sequences of the F1 or F2 fragments at the junction between the region overlapping P3 and P4, respectively. This is due, at least in part, to the addition of an extra adenosine base (A) at the 3' end of the PCR fragment by Taq DNA polymerase which is commonly used in PCR protocols. This could produce a mismatch between the PCR intermediate generated by P3/P4 and fragments F1 and F2.

Figure 2:
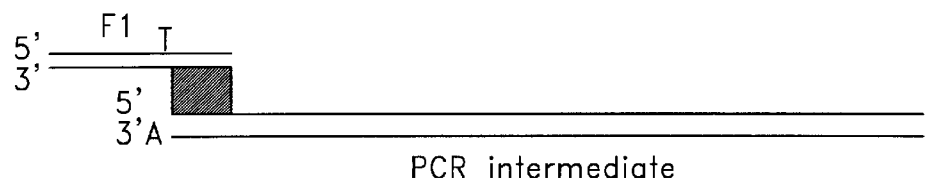
FIG. 2 is a schematic diagram showing DNA fragment F1 which contains a thymidine base immediately preceding the region of complementarity with the PCR intermediate (primer P3).

Thus, in a preferred embodiment, the overlap between the PCR intermediate (P3 primer) and F1, and P4/F2, is designed such that a thymidine base (T) immediately precedes the overlap region in fragments F1 and F2 (FIG. 2, only F1 shown). In this case, even with the addition of an "A" base to the 3' end to the intermediate during PCR amplification, the overlap between F1/F2 and the respective PCR intermediates is still perfectly maintained.

Peptide nucleic acids (PNA) are nucleic acid analogs in which the entire deoxyribose-phosphate backbone has been exchanged with a chemically completely different, but structurally homologous, polyamide (peptide) backbone containing 2-aminoethyl glycine units. Unlike DNA, which is highly negatively charged, the PNA backbone is neutral. Therefore, there is much less repulsive energy between complementary strands in a PNA-DNA hybrid than the comparable DNA-DNA hybrid, and consequently they are much more stable.

In addition, molecules called PNA "clamps" have been synthesized which have two identical PNA sequences joined by a flexible hairpin linker containing three 8-amino-3,6-dioxaoctanoic acid units. When a PNA clamp is mixed with a complementary homopurine or homopyrimidine DNA target sequence, a PNA-DNA-PNA triplex hybrid can form which is extremely stable (Bentin et al., *Biochemistry* 35:8863–8869, 1996; Egholm et al., *Nucleic Acids Res.* 23:217–222, 1995; Griffith et al., *J. Am. Chem. Soc.* 117:831–832, 1995). The sequence-specific and high affinity duplex and triplex binding of PNA have been extensively described (Nielsen et al., *Science* 254:1497–1500, 1991; Egholm et al., *J. Am. Chem. Soc.* 114:9677–9678, 1992; Egholm et al., Nature 365:566–568, 1993; Almarsson et al., *Proc. Natl. Acad. Sci. U. S. A.* 90:9542–9546, 1993; Demidov et al., *Proc. Natl. Acad. Sci. U. S A.* 92:2637–2641, 1995). They have also been shown to be resistant to nuclease and protease digestion (Demidov et al., *Biochem. Pharm.* 48:1010–1013, 1994).

A representative PNA clamp is shown in FIGS. 3 and 4. This PNA clamp, or a PNA clamp having any desired DNA sequence, is synthesized as described by Egholm et al. (supra.) or is available from PerSeptive Biosystems (Framingham, Mass.). The representative PNA clamp shown in FIGS. 2 and 3 has the sequence 5'-TCTCTCTC-O-O-O-TJTJTJTJ (SEQ ID NO: 1), where J (pseudoisocytosine) is an analog of C, and the "O" residues are 8-amino-3,6-dioxaoctanoic acid linkers which separate the two regions of the PNA.

The use of PNA tails, PNA clamps and PNA "clamp tails" to protect the ends of the transcriptionally active PCR fragments which are described above is illustrated in FIGS. 3 and 4. The ends of the PCR fragments generated as shown in FIG. 1 are prone to digestion by exonucleases after transfection into a cell or tissue. Two strategies for inhibiting this degradation are shown in FIGS. 3 and 4. In FIG. 3, a PNA tail and a short DNA sequence (5'-GATC-O-TCTCTCTC-3'; SEQ ID NO: 2) is added to the 5' end of primers P1 and P2 which bind to the target sequence 5'-GAGAGAGA-3' (SEQ ID NO: 3). This generates a PNA binding site at the 3' end of the opposite strand during PCR. Primers containing PNA tails can be synthesized using methods well known in the art or are available from Per-Septive Biosystems. These PNA tails do not hybridize to a target sequence, but protect the 5'-ends from exonuclease digestion. In order to protect the 5' ends of the PCR fragment, a PNA molecule is added to the 3' PNA tail-protected PCR fragment. This PNA contains a DNA sequence which is complementary to the 3'-end of the PCR fragment and binds thereto as shown in FIG. 3.

An alternate PNA protection approach is shown in FIG. 4. In this method, a PNA clamp is linked to primers P1 and P2 via one or more 8-amino-3,6-dioxaoctanoic acid linkers to form a PNA "clamp" tail by well known methods. After PCR amplification, the "clamp tail" binds to the 3' ends of the PCR fragment, and is linked to the 5' ends via the one or more 8-amino-3,6-dioxaoctanoic acid linkers to protect both the 3' and 3' ends of the PCR fragment.

Although the use of the CMV IE promoter and an artificial mammalian transcriptional terminator elements are exemplified herein, the use of any eukaryotic promoter and terminator is within the scope of the present invention. Suitable promoters for use in the present invention include, for example, SV40, rous sarcoma virus (RSV), retroviral long terminal repeats (LTR), muscle creatine kinase promoter, actin promoter, elongation factor promoter, synthetic promoters, tissue-specific promoters, and the like. Suitable terminator sequences include SV40 transcription terminator, bovine growth hormone (BGH) terminator, synthetic terminators, and the like. These promoter and terminator sequences can be obtained by restriction enzyme digestion of commercially available plasmids and cDNA molecules, or can be synthesized using an automated DNA synthesizer using methods well known in the art.

Any desired gene may be amplified and coupled to active promoter and terminator sequences using the method of the present invention. In a preferred embodiment, the gene encodes a gene product which is absent or present at reduced levels in an organism. Nonlimiting examples of these gene products are the cystic fibrosis transmembrane regulator (CFTR), insulin, dystrophin, interleukin-2, interleukin-12, erythropoietin, gamma interferon, and granulocyte macrophage colony stimulating factor (GM-CSF).

Although any transfection method well known in the art may be used to transfect the transcriptionally active PCR fragments of the invention into cells or tissues including calcium phosphate precipitation, electroporation and DEAE-dextran, cationic lipid-mediated transfection is preferred. Gene delivery systems are described by Feigner et al. (Hum. Gene Ther. 8:511–512, 1997) and include cationic lipid-based delivery systems (lipoplex), polycation-based delivery systems (polyplex) and a combination thereof (lipopolyplex). Cationic lipids are described in U.S. Pat. Nos. 4,897,355 and 5,459,127, the entire contents of which are hereby incorporated by reference.

EXAMPLE 1

Production of Transcriptionally Active PCR Fragments

The following components are combined in a 100 µl reaction volume: DNA fragment F1 (4 ng) which comprises a region of high transcriptional potency (−240 to +60) from the human cytomegalovirus (CMV) immediate early gene (IE) promoter/enhancer, DNA fragment F2 (4 ng), a 55 base pair oligonucleotide encoding an artificial mammalian transcription terminator element (5'-CACAAAAAACCA ACA-CACAGATCTCTAGAGCTCTGATCTTTTATTAGCCAG AAGT-3'; SEQ ID NO: 4), 400 ng primer P1 (5'-TCTCTCTACGTATTAGTCATCG-3'; SEQ ID NO: 5), 400 ng primer P2 (5'-TCACAAAAAACCAACACACAG-3'; SEQ ID NO: 6), 4 ng primer P3 and 4 ng primer P4. The P1 and P2 primer sequences correspond to the 5' end of fragment F1 and the 5' end of fragment F2, respectively (FIG. 1). Primers P3 and P4 are designed based on the gene sequence of interest. The 3' potion of these primers (about 10–20 base pairs) is determined by the actual sequence of the gene to be amplified, whereas the 5' region of P3 comprises the following sequence: 5'-CTCCGCGGATCCAGA-3' (SEQ ID NO: 7) to overlap with the 3' region of F1, and P4 comprises the sequence 5'-TTATTAGCCAGAAGT-3' (SEQ ID NO: 8) to overlap with the 3' region of F2.

PCR is performed as follows: denaturation for 30 seconds at 94° C., annealing for 45 seconds at 55° C. and extension for three minutes at 72° C. for 25–30 cycles. The size of the final produce is verified by 1% agarose gel electrophoresis. The amplified PCR fragment is cleaned and purified using a commercial PCR cleaning kit (e.g., Qiagen), and can be used for in vitro or in vivo transfection of cells or tissues.

EXAMPLE 2

The green fluorescent protein (GFP, 700 bp) was used as a target gene. The F1 fragment was a 600 bp fragment of the CMV immediate early gene promoter (from −550 to +50). A 50 bp oligonucleotide containing a modified rabbit beta-globin gene transcription terminator was used as primer 2. Two different versions of these primers were designed so that the overlap between F1 and the intermediate GFP PCR fragment was either preceded with or without a thymidine base. After the PCR reaction was carried out according to the conditions described in Example 1, the products were analyzed by electrophoresis. When a thymidine base preceded the overlap region in F1, a clean major PCR fragment of about 1.4 kb was produced, representing the GFP coding region flanked by CMV promoter (F1) and the transcription terminator, whereas if a base other than thymidine preceded the overlapping region, no product was generated. The fragment generated by nested PCR was then transfected into Cos-7 cells and the expression of GFP was monitored by fluorescence microscopy. The results showed that the intensity and frequency of GFP-expressing cells was almost the same between cells transfected with the PCR fragment and a supercoiled plasmid DNA in which the same CMV promoter was driving expression of the GFP gene. Thus, the present method produces DNA fragments which are transcriptionally active.

While particular embodiments of the invention have been described in detail, it will be apparent to those skilled in the art that these embodiments are exemplary rather than limiting, and the true scope of the invention is that defined in the following claims.

What is claimed is:

1. A method of generating a transcriptionally active DNA molecule, comprising polymerase chain reaction (PCR) amplification of said DNA molecule in the presence of a first DNA fragment (F1), second DNA fragment (F2), first primer (P1), a second primer (P2), a third primer (P3), and a fourth primer (P4) wherein:

F1 comprises a promoter sequence;

F2 comprises a terminator sequence;

P1 is complementary to the 5' end of F1;

P2 is complementary to the 5' end of F2;

P3 comprises a first region complementary to the 3' end of F1 and a second region complementary to the 5' end of said DNA molecule, wherein a thymidine base immediately precedes said region of complementarity between said third primer P3 and said first DNA fragment F1; and P4 comprises a first region complementary to the 3' end of F2 and a second region complementary to the 3' end of said DNA molecule, whereby a transcriptionally active DNA molecule is produced by said PCR amplification.

2. The method of claim 1, wherein F1 is the cytomegalovirus IE promoter.

3. The method of claim 1, wherein said transcriptionally active DNA molecule encodes a therapeutic gene.

4. The method of claim 1, further comprising the step of adding a PNA tail to the 5'-end of P1 and P2 prior to said PCR amplification.

5. The method of claim 1, further comprising the step of adding a PNA clamp to said transcriptional active DNA molecule after said PCR amplification.

6. The method of claim 1, further comprising the step of adding a PNA molecule via a linker to primers P1 and P2 prior to said PCR amplification.

7. A method of generating a transcriptionally active DNA molecule, comprising polymerase chain reaction (PCR) amplification of said DNA molecule in the presence of a first DNA fragment (F1), second DNA fragment (F2), first primer (P1), a second primer (P2), a third primer (P3), and a fourth primer (P4) wherein:

F1 comprises a promoter sequence;

F2 comprises a terminator sequence;

P1 is complementary to the 5' end of F1;

P2 is complementary to the 5' end of F2;

P3 comprises a first region complementary to the 3' end of F1 and a second region complementary to the 5' end of said DNA molecule; and P4 comprises a first region complementary to the 3' end of F2 and a second region complementary to the 3' end of said DNA molecule, wherein a thymidine base immediately precedes said region of complementarity between said fourth primer P4 and said second DNA fragment F2, whereby a transcriptionally active DNA molecule is produced by said PCR amplification.

8. The method of claim 7, wherein F1 is the cytomegalovirus IE promoter.

9. The method of claim 7, wherein said transcriptionally active DNA molecule encodes a therapeutic gene.

10. The method of claim 7, further comprising the step of adding a PNA tail to the 5'-end of P1 and P2 prior to said PCR amplification.

11. The method of claim 7, further comprising the step of adding a PNA clamp to said transcriptionally active DNA molecule after said PCR amplification.

12. The method of claim 7, further comprising the step of adding a PNA molecule via a linker to primers P1 and P2 prior to said PCR amplification.

* * * * *

UNITED STATES PATENT AND TRADEMARK OFFICE
CERTIFICATE OF CORRECTION

PATENT NO. : 6,280,977 B1 Page 1 of 1
DATED : August 28, 2001
INVENTOR(S) : Liang et al.

It is certified that error appears in the above-identified patent and that said Letters Patent is hereby corrected as shown below:

Column 7,
Line 19, please change "transcriptional," to -- transcriptionally --.

Signed and Sealed this

Nineteenth Day of August, 2003

JAMES E. ROGAN
*Director of the United States Patent and Trademark Office*